United States Patent
Yang

[11] Patent Number: 6,046,367
[45] Date of Patent: Apr. 4, 2000

[54] TRIPHENYLBIS (FLUOROALKOXY) PHOSPHORANES AND FLUORINATED KETALS

[75] Inventor: Zhen-Yu Yang, Wilmington, Del.

[73] Assignee: E. I. du Pont de Nemours and Company, Wilmington, Del.

[21] Appl. No.: 08/320,624

[22] Filed: Oct. 7, 1994

Related U.S. Application Data

[63] Continuation of application No. 08/029,087, Mar. 10, 1993, abandoned.

[51] Int. Cl.⁷ .................................................... C07C 43/313
[52] U.S. Cl. ............................................ 568/604; 568/596
[58] Field of Search ...................................... 568/604, 596

[56] References Cited

U.S. PATENT DOCUMENTS

| | | | |
|---|---|---|---|
| 2,901,514 | 8/1959 | Drysdale | 568/604 |
| 3,029,252 | 4/1962 | Simmons | 568/604 |
| 3,883,663 | 5/1975 | Moore et al. | 568/604 |
| 4,067,886 | 1/1978 | Reardon et al. | 568/604 |
| 4,943,595 | 7/1990 | Scherer et al. | 568/604 |
| 5,202,480 | 4/1993 | Bierschenk et al. | 568/604 |

FOREIGN PATENT DOCUMENTS

WO 90/3357  4/1990  WIPO ................................ 568/604

OTHER PUBLICATIONS

Lowthere, N. et al, *J. chem. Soc., Chem. Comm.*, 1303 91985).
Von Itzstein, M. et al, *Aust, J. Chem.*, 36, 557 (1983).
Denney, D.B. et al, *J. Am. Chem. Soc.*, 103, 1785 (1981).
Kubota, T. et al, *J. Org. Chem.*, 45, 5052 (1980).
Shermalovich, Yu. G. et al, *Zh. Org. Khim*, 52, 2526 (1982).
Kubota, T. et al, *Chemistry Letters*, pp. 845–846.

*Primary Examiner*—James H. Reamer

[57] ABSTRACT

Novel triphenylbis(fluoroalkoxy)phosphoranes and a process for their preparation are disclosed. Also disclosed is a process for making fluorinated ketals by reacting phosphoranes with fluorinated ketones.

3 Claims, No Drawings

TRIPHENYLBIS (FLUOROALKOXY) PHOSPHORANES AND FLUORINATED KETALS

This is a continuation of application Ser. No. 08/029,087, filed Mar. 10, 1993 now abandoned.

FIELD OF THE INVENTION

Novel triphenylbis(fluoroalkoxy)phosphoranes are disclosed. Also disclosed are fluorinated ketals made from these phosphoranes with fluorinated ketones and a process for their preparation.

TECHNICAL BACKGROUND

One triphenylbis(fluoroalkoxy)phosphorane, $Ph_3P(OCH_2CF_3)_2$, has been disclosed in the literature. See the following references a–d:

a) N. Lowther and C. D. Hall, J. Chem. Soc., Chem. Comm., 1303 (1985) describe the preparation of $Ar_3P(OCH_2CF_3)_2$ (Ar=substituted phenyl rings) by the reaction of $Ar_nP(OR)_{n-3}$ (n=0 to 3) with $PhSOCH_2CF_3$ and the mechanisms in the hydrolysis of these phosphoranes.

b) M. Von Itzstein and I. D. Jenkins, Aust, J. Chem., 36, 557 (1983), disclose a method for the preparation of dialkoxytriphenylphosphoranes by the reaction of $Ph_3P$ with alcohols in the presence of azodicarboxylates and the mechanism for this reaction. This paper deals mainly with hydrocarbon phosphoranes and only one fluorinated compound $Ph_3P(OCH_2CF_3)2$ was described. The fluorinated compound is prepared either by their new method or reaction of $Ph_3PBr_2$ and $CF_3CH_2OH$ in the presence of $Et_3N$. The later reaction is the same as that used herein.

c) D. B. Denney et al., J. Am. Chem. Soc., 103, 1785 (1981) report the preparation of phosphoranes containing the trifluoroethoxy group and the reaction of these fluorinated phosphoranes with alkoxides such as trifluoroethoxide.

d) T. Kubota et al., J. Org. Chem., 45, 5052 (1980) used bis (2,2,2-trifluoroethoxy)triphenyl- phosphorane as a condensation reagent for alcohols with thiols. The preparation of $Ph_3P(OCH_2CF_3)_2$ and application of this reagent in organic synthesis is described in detail. These researchers prepared $Ph_3P(OCH_2CF_3)_2$ from the reaction of $Ph_3PBr_2$ and $NaOCH_2CF_3$ and investigated the reactions of $Ph_3P(OCH_2CF_3)2$ with alcohols, carboxylic acid, thiols and amines. This reference also mentions the reaction of $Ph_3P(OCH_2CF_3)_2$ with hydrocarbon aldehydes to give the corresponding acetals.

e) Yu. G. Shermalovich et al., Zh. Org. Khim, 52, 2526 (1982) report that $(CF_3)_2C(OCH_2CF_2CF_2H)_2$ has been prepared from the reaction of hexafluoroacetone (HFA) and $P(OCH_2CF_2CF_2H)_5$ The reaction of $P(OCH_2Rf)_5$ (Rf=$((CF_2)nH$, n=2,4) with carbonyl compounds is reported. Although the one mentioned fluorinated ketal, $(CF_3)_2C(CH_2CF_2CF_2H)_2$, was prepared by reaction of $P(OCH_2CF_2CF_2H)_5$ with hexafluoroacetone, the starting material used was different from that used herein; applicant's starting material is $Ph_3P(OCH_2Rf)_2$. Applicant believes that the method reported could not be adapted to prepare $(CF_3)_2(OCH_2CF_3)_2$ by the reaction of HFA with $P(OCH_2CF_3)_5$.

SUMMARY OF THE INVENTION

Novel triarylbis(fluoroalkoxy)phosphoranes, 1, $Ar_3P(OCH_2Rf)_2$  1 are disclosed. In formula 1, Ar is phenyl (hereinafter Ph) or Ph substituted with alkyl or other substituents that are selected so as not to interfere with the process reaction. $R_f$ is a perfluoroalkyl group, a perfluoroalkenyl group or a perfluoroalkynyl group of 1 to 20 carbon atoms, optionally substituted by one or more chlorine or hydrogen atoms, and optionally containing one or more oxygen atoms. The perfluoroalkyl group, perfluoroalkenyl group or perfluoroalkynyl group may be straight chain or branched, provided, however, that $R_f$ is not $CF_3$.

Preferred $R_f$ groups are selected from the group consisting of $CF_2Cl$, $CF_2CF_3$, $CFClCF_2Cl$, and $CF_2=CFOCF_2CF(CF_3)OCF_2CF_2$.

Also disclosed is a process for making fluorinated ketals of the formula 2 from phosphoranes of formula 1 by reaction of these phosphoranes with fluorinated ketones.

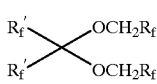

2

In formula 2:

$R_f$ is a perfluoroalkyl group, a perfluoroalkenyl group or a perfluoroalkynyl group of 1 to 20 carbon atoms, optionally substituted by one or more chlorine atoms, and optionally containing one or more oxygen atoms. The perfluoroalkyl group, perfluoroalkenyl group or perfluoroalkynyl group may be straight chain or branched. Preferred $R_f$ groups are selected from the group consisting of $CF_2Cl$, $CF_2CF_3$, $CFClCF_2Cl$, and $CF_2=CFOCF_2CF(CF_3)OCF_2CF_2$. $R_f'$ is a straight chain or branched perfluoroalkyl group, a perfluoroalkenyl group or a perfluoroalkynyl group of 1 to 20 carbon atoms, optionally substituted by one or more hydrogen atoms and optionally containing one or more oxygen atoms.

Preferred $R_f'$ groups are $C_1$ to $C_{20}$ perfluoroalkyl. Especially preferred are $CF_3$ and $CF_2CF_3$.

The process for the preparation of various triphenylbis(fluoroalkoxy)phosphoranes involves the reaction of triphenylphosphine dibromide and the corresponding fluoroalcohols in the presence of a tertiary amine.

The triphenylbis(fluoroalkoxy)phosphorane product of this reaction can then be used to prepare fluorinated ketals when reacted with the corresponding ketones, as shown below.

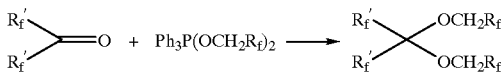

wherein $R_f$ and $R_f'$ are as defined above. The process can be conducted neat or in the presence of a solvent for one or both of the reagents, within a temperature range of about 20° C. to about 250° C.

DETAILED DESCRIPTION OF THE INVENTION

Although a number of triphenylbis(alkoxy)phosphoranes, $Ph_3P(OCH_2R)_2$, have been reported in the literature, the preparation of only one triphenylbis(fluoroalkoxy)phosphorane, $Ph_3P(OCH_2CF_3)_2$, is known. The preparation of this fluorinated phosphorane was achieved by the reaction of $Ph_3P$ with either $CF_3CH_2OH$, in the presence of diethyl azodicarboxylate, or trifluoroethyl benzenesulfonate. $Ph_3P(OCH_2CF_3)_2$ can also be prepared by reaction of $Ph_3PBr_2$ and $NaOCH_2CF_3$. References for these various methods are listed in the Technical Background on page 1, herein.

An efficient process for the preparation of various triphenylbis(fluoroalkoxy)phosphoranes involves reaction of triphenylphosphine dibromide and the corresponding fluoroalcohols in the presence of a tertiary amine (e.g., triethylamine), as shown by the example, below, where $R_f$ is a perfluoroalkyl group, a perfluoroalkenyl group or a perfluoroalkynyl group of 1 to 20 carbon atoms, optionally substituted by one or more chlorine or hydrogen atoms, and optionally containing one or more oxygen atoms. The perfluoroalkyl group, perfluoroalkenyl group or perfluoroalkynyl group may be straight chain or branched. Preferred $R_f$ groups are selected from the group consisting of $CF_2Cl$, $CF_2CF_3$, $CFClCF_2Cl$, and $CF_2=CFOCF_2CF(CF_3)OCF_2CF_2$.

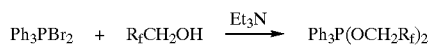

$Ph_3P(OCH_2Rf)_2$ can then be reacted with the corresponding ketones to produce fluorinated ketals.

There appear to be no universal methods for the preparation of fluorinated ketals of the formula $(R_f')_2C(OCH_2Rf)_2$. As indicated in the Technical Background, above, one fluorinated ketal, $(CF_3)_2C(OCH_2CF_2CF_2H)_2$, has been reported, which was prepared from the reaction of hexafluoroacetone (HFA) and $P(OCH_2CF_2CF_2H)_5$. However, that reported method for making $(CF_3)_2C(OCH_2CF_2CF_2H)_2$ was found not to extend to prepare $(CF_3)_2C(OCH_2CF_3)_2$ by the reaction of HFA with $P(OCH_2CF_3)_5$.

The present process can be carried out neat (no solvent) or in the presence of aprotic solvents such as, but not limited to, dichloromethane, 1,1,2-trifluoro-trichloroethane, ether, acetonitrile, dimethylformamide (DMF), benzene, toluene and chlorobenzene.

The process is carried on at temperatures from ambient (about 20° C.) to about 250° C. A preferred temperature range is about 100° C. to about 200° C. It is most preferred to conduct the process at about 150° C. to about 200° C. There are no specific pressure requirements. Autogeneous pressure is sufficient.

The fluorinated ketals produced are useful synthetic intermediates for fluorocarbon compounds and as monomers for fluoropolymers.

EXAMPLE 1

Synthesis of $Ph_3P(OCH_2CF_3)_2$

To a stirred solution of 136.2 g (0.52 mol) of $Ph_3P$ in 300 mL of of $CH_2Cl_2$ was added a solution of 41.6 g (0.52 mol) of $Br_2$ in 100 mL of $CH_2Cl_2$ at −40° C. over 1 hour. After the addition was complete, the mixture was stirred at −40° C. to room temperature for 1 hour and then cooled to −40° C. A mixture of 100 g (1.0 mol) of $CF_3CH_2OH$ and 101.0 g (1 mol) of $Et_3N$ in 400 mL of ether was added at this temperature over 1 hour and then the resulting reaction mixture was warmed to room temperature and stirred for an additional 3.5 hours. After the solids were removed by filtration under nitrogen, the filtrate was evaporated under vacuum at room temperature to give solids 209.3 g (91%). Analytic sample was obtained by slow evaporation of $CH_2Cl_2$ and pentane solution. mp 138.4. $^1H$ NMR($CDCl_3$): 8.11–8.04 (m, 6H), 7.57–7.33 (m, 9H), 2.88 (qd, J=8.9 Hz, J=4.2 Hz, 4H); $^{19}F$ NMR($CDCl_3$): −74.7 (t, J=8.9 Hz); $^{31}P$ NMR($CH_2Cl_2$): −58.0 (s). Calcd. for $C_{22}H_{19}F_6PO_2$: C, 57.40; H, 4.16; F, 24.76; P, 6.73. Found: C, 57.27; H, 4.32; F, 24.91; P, 7.06.

EXAMPLE 2

Synthesis of $Ph_3P(OCH_2CF_2Cl)_2$

A similar experiment using 30.0 g (0.115 mol) of $Ph_3P$, 18.3 g (0.115 mol) of $Br_2$, 25.0 g (0.21 mol) of $ClCF_2CH_2OH$ and 21.2 g (0.21 mol) of $Et_3N$ in 100 mL of ether and 100 mL of $CH_2Cl_2$ gave 50.1 g (96.7%) of $Ph_3P(OCH_2CF_2Cl)_2$. $^1H$ NMR($CDCl_3$): 8.14–8.06 (m, 6H), 7.71–7.49 (m, 9H), 3.00 (td J=11.1 Hz, J=3.8 Hz, 4H); $^{19}F$ NMR: −61.2 (t, J=11.0 Hz); 31P NMR($CH_2Cl_2$) −57.7 (s). Analytic sample was obtained by slow evaporation of solution in $CH_2Cl_2$ and pentane. Calcd. for $C_{22}H_{19}F_4Cl_2PO_2$: C, 53.57; H, 3.88; F, 15.41; Cl, 14.37; P, 6.28. Found: C, 53.55; H, 4.19; F, 17.39; Cl, 13.33, P, 6.84.

EXAMPLE 3

Synthesis of $Ph_3P(OCH_2CF_2CF_3)_2$

A similar experiment using 52.4 g (0.2 mol) of $Ph_3P$, 32.0 g (0.2 mol) of $Br_2$, 60.0 g (0.4 mol) of $CF_3CF_2CH_2OH$ and 41.8 g of $Et_3N$ in 150 mL of $CH_2Cl_2$ and 200 mL of ether gave 105.1 g (94%) of $Ph_3P(OCH_2CF_2CF_3)_2$. $^1H$ NMR ($CDCl_3$): 8.07–8.01 (m, 6H), 7.54–7.33 (m, 9H), 2.95 (td, J=13.1 Hz, J=2.8 Hz, 4H); $^{19}F$ NMR($CDCl_3$): −83.7 (s, 6F), −123.7 (t, J=13.2 Hz, 4F); $^{31}P$ NMR($CH_2Cl_2$): −57.2 (s).

EXAMPLE 4

Synthesis of $Ph_3P(OCH_2CF_2CF_2H)_2$

A similar experiment using 52.4 g (0.2 mol) of $Ph_3P$, 32.0 g (0.2 mol) of $Br_2$, 54.1 g (0.41 mol) of $HCF_2CF_2CH_2OH$ and 41.4 g (0.41 mol) of $Et_3N$ in 250 mL of $CH_2Cl_2$ and 250 mL of ether gave 96.6 g (92%) of $Ph_3P(OCH_2CF_2CF_2H)_2$. $^1H$ NMR($CDCl_3$): 8.04–9.76 (m, 4H), 7.52–7.48 (m, 9H), 5.74 (tt, J=53.4 Hz, J=5.5 Hz, 2H); $^{19}F$ NMR($CDCl_3$): −126.5 (m, 4F), −141.2 (t, J=54 Hz, 4F); $^{31}P$ NMR($CH_2Cl_2$): −56.0 (s).

EXAMPLE 5

Synthesis of $Ph_3P(OCH_2CFClCF_2Cl)_2$

A similar experiment using 21.0 g (0.08 mol) of $Ph_3P$, 12.8 g (0.08 mol) of $Br_2$, 27.0 g (0.147 mol) of $ClCF_2CFClCH_2OH$ and 15.0 g (0.148 mol) of $Et_3N$ in 100 mL of $CH_2Cl_2$ and 100 mL of ether gave 38.1 g (83%) of $Ph_3P(OCH_2CFClCF_2Cl)_2$. $^1H$ NMR($CDCl_3$): 8.11–8.03 (m, 6H), 7.50–7.32 (m, 9H), 3.11 (dd, J=24.6 Hz, J=3.5 Hz, 4H); $^{31}P$ NMR($CH_2Cl_2$): −56.4 (s).

EXAMPLE 6

Synthesis of $Ph_3P[OCH_2(CF_2)_4H]_2$

A similar experiment using 78.6 g (0.3 mol) of $Ph_3P$, 48 g (0.3 mol) of $Br_2$, 140.0 g (0.6 mol) of $H(CF_2)_4CH_2OH$ and 61.0 g (0.6 mol) of $Et_3N$ in 300 mL of $CH_2Cl_2$ and 300 mL of ether gave 196.7 g (90%) of $Ph_3P[OCH_2(CF_2)_4H]_2$. $^1H$ NMR($CDCl_3$): 8.09–8.01 (m, 6H), 7.66–7.47 (m, 9H), 5.88 (tt, J=52.0 Hz, J=5.6 Hz, 2H), 3.02 (td, J=14.0 Hz, J=3.9 Hz); $^{19}F$ NMR: −119.7 (t, J=11.6 Hz, 4F), −125.8 (s, 4F), −131.2 (m, 4F), −138.0 (d, J=52.0 Hz, 4F); $^{31}P$ NMR ($CH_2Cl_2$): −55.5 (s).

EXAMPLE 7

Synthesis of $Ph_3P(OCH_2CF_2CF_2OCF_2CFCF_3OCF=CF_2)_2$

A similar experiment using 22.0 g (0.084 mol) of $Ph_3P$, 13.4 g (0.084 mol) of $Br_2$, 59.5.0 g (0.15 mol) of $CF_2=$ CFOCF$_2$CF(CF$_3$)OCF$_2$CF$_2$CH$_2$OH (EVEOH) and 15.2 g (0.15 mol) of Et$_3$N in 100 mL of CH$_2$Cl$_2$ and 100 mL of ether gave 59.6 g (75.3%) of Ph$_3$P(OEVE)$_2$. $^1$H NMR (CDCl$_3$): 8.08–8.01 (m, 6H), 7.48–7.32 (m, 9H), 2.95 (td, J=13.7 Hz, J=4.0 Hz, 4H). $^{19}$F NMR(CDCl$_3$): –80.3 (s, 6F), –83.9 (m, 4F), –85.1 (m, 4H), –113.9 (dd, J=83.8 Hz, J=65.6 Hz, 2F), –122.1 (dd, J=112.3 Hz, J=83.8 Hz, 2F), –123.2 (t, J=13.8 Hz, 4F), –135.6 (dd, J=112.3 Hz, J=65;5 Hz, 2F), –145.4 (t, J=21.9 Hz, 2F). $^{31}$P NMR (CH2Cl2): –56.2 (s).

EXAMPLE 8

Synthesis of (CF$_3$)$_2$C(OCH$_2$CF$_3$)$_2$

A solution of 420 g of Ph$_3$P(OCH$_2$CF$_3$)$_2$ in 300 mL of CH$_2$Cl$_2$ was transferred into a 1 L autoclave under N$_2$ and then pressured with 180 g of hexfluoroacetone. After being heated at 150° C. for 3 hours and 200° C. for 4 hours, the reaction mixture was poured into a flask and distilled to give the desired product 208.9 g, bp 95.5–96° C., 99.8% purity. $^{19}$F NMR(CDCl$_3$): –75.1 (t, J=7.5 Hz, 6F), –76.1 (s, 6F); $^1$H NMR(CDCl$_3$): 4.18 (q, J=7.7 Hz). Anal: Calcd. for C$_7$H$_4$F$_{12}$O$_2$: C, 24.15; H, 1.16; F, 65.49. Found: C, 24.21; H, 1.49; F, 65.53.

EXAMPLE 9

Synthesis of (CF$_3$)$_2$C(OCH$_2$CF$_2$CF$_3$)$_2$

A mixture of 95 g of Ph$_3$P(OCH$_2$CF$_2$CF$_3$)$_2$ and 34 g of hexafluoroacetone in 120 mL of CH$_2$Cl$_2$ was heated in shaker tube at 150° C. for 3 hours and at 210° C. for 2 hours. Two layers were observed and the lower layer was separated and distilled to give 55.3 g of desired product (99% purity). bp 120–121° C. $^{19}$F NMR(CDCl$_3$): –76.0 (s, 6F), –84.4 (s, 6F), –124.7 (t, J=11.8 Hz, 4F); $^1$H NMR(CDCl$_3$): 4.22 (t, J=8.0 Hz). Anal: Calcd. for C$_9$H$_4$F$_{16}$O$_2$: C, 24.12; H, 0.90. Found: C, 24.48; H, 1.04.

EXAMPLE 10

Synthesis of (CF$_3$)$_2$C(OCH$_2$CF$_2$CF$_2$H)$_2$

A mixture of 84 g of Ph$_3$P(OCH$_2$CF$_2$CF$_2$H)$_2$ and 27 g of hexafluoroacetone in 100 mL of CH$_2$Cl$_2$ was heated in shaker tube at 150° C. for 6 hours. After evaporation of the CH$_2$Cl$_2$, the residue was distilled under partial vacuum (30 mmHg) to give 56.8 g of crude product (88% purity). Redistillation gave 36.8 g pure product (99.8% purity), bp 72° C./30 mmHg). $^{19}$F NMR (CDCl$_3$): –75.9 (s, 6F), –124.7 (t, J=12.2 Hz, 4F), –138.4 (d, J=53.0 Hz, 4F); $^1$H NMR (CDCl$_3$): 5.92 (tt, J=53.0 Hz, J=3.8 Hz, 2H), 4.20 (t, J=12.0 Hz, 4H).

EXAMPLE 11

Synthesis of (CF$_3$CF$_2$)$_2$C(OCH$_2$CF$_3$)$_2$

A mixture of 23 g of Ph$_3$P(OCH$_2$CF$_3$)$_2$ and 13.3 g of perfluoropentanone-3 in 30 mL of CH$_2$Cl$_2$ was heated in shaker tube at 150° C. for 3 hours and 210° C. for 3 hours. After evaporation of the CH$_2$Cl$_2$, the residue was distilled under partial vacuum (–30 mmHg) to give 7.2 g of crude product. Redistillation gave 6.8 g of pure product, bp 125–128° C. $^{19}$F NMR(CDCl$_3$): –74.4 (t, J=7.5 Hz, 6F), –79.0 (s, 6F), –117.2 (s, 4F), $^1$H NMR (CDCl$_3$): –4.27 (q, J=7.6 Hz). Anal.: Calcd. for C$_9$H$_4$F$_{16}$O$_2$: C, 24.12; H, 0.90; F, 67.84. Found: C, 24.45; H, 0.95; F, 67.04.

EXAMPLE 12

Synthesis of (CF$_3$)$_2$C(OCH$_2$CF$_2$CF$_2$CF$_2$CF$_2$H)$_2$

A mixture of 74 g of Ph$_3$P(OCH$_2$CF$_2$CF$_2$CF$_2$CF$_2$H)$_2$ containing 16% H(CF$_2$)$_4$CH$_2$OH and 33.2 g of HFA in 70 mL of CH$_2$Cl$_2$ was heated in shaker tube at 150° C. for 3 hours and 210° C. for 3 hours. After evaporation of the CH$_2$Cl$_2$, the residue was distilled to give 28.8 g of product with 89% purity. Redistillation gave 21.0 g of pure product, bp 85° C./5 mmHg. $^{19}$F NMR(CDCl$_3$): –76.0 (s, 6F), –121.1 (t, J=11.6 Hz, 4F), 125.7 (s, 4F), –130.4 (s, 4F), –137.8 (d, J=50.1 Hz, 4F). Anal: Calcd. for C$_{13}$H$_6$F$_{22}$O$_2$: C, 25.51; H, 0.99; F, 68.28. Found: C, 25.68; H, 1.05; F, 68.01.

EXAMPLE 13

Synthesis of (CF$_3$)$_2$C(OEVE)$_2$

A mixture of 59.6 g of Ph$_3$P(OEVE)$_2$, 13.0 g of HFA in 30 mL of CH$_2$Cl$_2$ was heated in shaker tube for 6 hours. The reaction mixture was poured into a jar and the lower layer was separated and distilled under reduced pressure to give 8.5 g of (CF$_3$)$_2$C(OEVE)$_2$. bp 65–66° C./0.3 mmHg. $^1$H NMR: 4.54 (t, J=12.4 Hz), $^{19}$F NMR: –75.7 (s, 6F), –80.0 (f, J=7.4 Hz, 6F), –83.3 (m, 4F), –84.7 (m, 4F), –113.3 (dd, J=85.0 Hz, J=65.6 Hz, 2F), –121.8 (dd, J=111.8 Hz, J=85.0 Hz, 2H), –123.5 (t, J=12.3 Hz, 4F), –136.1 (ddt, J=111.8 Hz, J=65.5 Hz, J=5.6 Hz, 2F), –145.2 (t, J=21.9 Hz, 2F). IR (neat): 2976 (w), 1839 (m), 1342 (s), 1315 (s), 1234 (s), 1162 (s). HRMS: Calcd. for C$_{18}$H$_4$F$_{29}$O$_6$ (M-CF3): 867.1826. Found: 866.9549.

COMPARATIVE EXAMPLE 1

A. Synthesis of P(OCH$_2$CF$_3$)$_5$

A 1 L three-necked flask fitted with a mechanical stirrer, a condenser and an addition funnel was charged with 62.6 g of PCl$_5$ and 600 mL of anhydrous ether. The mixture was cooled at –40° C. and a solution of 155 g of CF$_3$CH$_2$OH, 165 g of Et$_3$N in 400 mL of ether was added over 1.5 hours. After the addition was complete, the resulting mixture was stirred at –40° C. to room temperature overnight. Solids were removed by filtration under nitrogen and washed with ether. After evaporation of the ether, residue was distilled to give 126.3 g of desired product, bp 81–82° C./9 mmHg. $^{19}$F NMR (CDC13): –76.0 (t, J=8.3 Hz); $^1$H NMR (CDCl$_3$): 4.20 (qd, J=7.1 Hz, J=7.1 Hz); $^{13}$C NMR: 123.75 (qd, J=276.7 Hz, J=13.0 Hz), 63.38 (qd, J=36.4 Hz, J=10.8 Hz). $^{31}$P NMR: –76.3 (s).

B. Reaction of P(OCH$_2$CF$_3$)$_5$ with hexafluoroacetone

A mixture of 62.6 g of P(OCH$_2$CF$_3$)$_5$ and 16.6 g of hexafluoroacetone was heated at 150° C. in shaker tube for 8 hours. No desired product was obtained and only P(OCH$_2$CF$_3$)$_5$ was recovered. When the above reaction was carried out at 210° C. for 8 hours and at 250° C. for 5 hours, no reaction was observed.

What is claimed is:

1. A ketal of the formula:

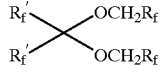

wherein R$_f$ is selected from straight chain or branched perfluoroalkyl, perfluoroalkenyl, perfluoroalkynyl, perfluoroalkoxy, perfluoroalkenoxy, perfluorochoroalkyl, perfluorochloroalkenyl, perfluorochloroalkynyl, perfluorochloroalkoxy, and perfluorochloroalkenoxy of 1–20 carbon atoms, and R$_f'$ is a straight chain or branched perfluoroalkyl group, a perfluoroalkenyl group, a perfluoroalkynyl group, a perfluoroalkoxy group, a perfluoroalkenoxy group, a fluoroalkyl group, a fluoroalkenyl group, a fluoroalkynyl group, a fluoroalkoxy group, or a fluoroalkenoxy group of 1 to 20 carbon atoms.

2. The ketal compound as described by claim 1 wherein $R_f$ is selected from $CF_2Cl$, $CF_2CF_3$, $CFClCF_2Cl$, and $CF_2=CFOCF_2CF(CF_3)OCF_2CF_2$.

3. The ketal compound, as described in claim 1, wherein $R_f'$ is a $C_1$ to $C_{20}$ perfluoroalkyl.

* * * * *